(12) United States Patent
Mayer et al.

(10) Patent No.: US 10,765,469 B2
(45) Date of Patent: Sep. 8, 2020

(54) METHOD FOR PRODUCING A BRANCH AND SURGICAL INSTRUMENT COMPRISING A TOOL HAVING A BRANCH

(71) Applicant: ERBE ELEKTROMEDIZIN GMBH, Tuebingen (DE)

(72) Inventors: Volker Mayer, Tuebingen (DE); Achim Brodbeck, Metzingen (DE)

(73) Assignee: ERBE ELEKTROMEDIZIN GMBH, Tuebingen (DE)

( * ) Notice: Subject to any disclaimer, the term of this patent is extended or adjusted under 35 U.S.C. 154(b) by 1224 days.

(21) Appl. No.: 14/816,656

(22) Filed: Aug. 3, 2015

(65) Prior Publication Data

US 2016/0030105 A1    Feb. 4, 2016

(30) Foreign Application Priority Data

Aug. 4, 2014  (EP) .................................... 14179742

(51) Int. Cl.
  *B22F 3/105* (2006.01)
  *A61B 18/14* (2006.01)
  (Continued)

(52) U.S. Cl.
  CPC ........ *A61B 18/1445* (2013.01); *B22F 3/1055* (2013.01); *B22F 3/225* (2013.01); *B22F 7/08* (2013.01); *B23K 26/342* (2015.10); *B29C 45/14377* (2013.01); *A61B 2017/00526* (2013.01); *A61B 2018/00589* (2013.01);
  (Continued)

(58) Field of Classification Search
  CPC ............ B29C 45/14377; A61B 18/085; A61B 18/1442; A61B 18/1445; A61B 18/1447; A61B 2018/0225; A61B 2018/0231; A61B 2018/0237; A61B 2018/0243; A61B 2018/025; A61B 2018/0256; A61B 2018/0262; A61B 2018/0268;
  (Continued)

(56) References Cited

U.S. PATENT DOCUMENTS 5,462,622 A * 10/1995 Small ................ B29C 45/14639
    156/245
2008/0195093 A1 * 8/2008 Couture ............. A61B 18/1445
    606/45
(Continued)

FOREIGN PATENT DOCUMENTS

AU    2011226904 A1    4/2012
AU    2011226904 B2    4/2012
(Continued)

OTHER PUBLICATIONS

Frazier, William E., "Metal Additive Manufacturing: A Review," Journal of Materials Engineering and Performance, vol. 23(6), Jun. 2014, pp. 1917-1928. (Year: 2014).*

*Primary Examiner* — Vanessa T. Luk
(74) *Attorney, Agent, or Firm* — Blank Rome LLP

(57) ABSTRACT

A branch is produced by means of an additive 3D production process for producing a metal part, which comprises at least two parts, namely a support section and a functional section. The metal part is a single-pieced part, in which the support section and the functional section are seamlessly interconnected by means of corresponding connecting webs. After the material is applied, the connecting webs are removed.

4 Claims, 2 Drawing Sheets

(51) Int. Cl.
*B23K 26/342* (2014.01)
*B22F 7/08* (2006.01)
*B29C 45/14* (2006.01)
*B22F 3/22* (2006.01)
*A61B 18/00* (2006.01)
*A61B 17/00* (2006.01)
*B33Y 10/00* (2015.01)
*B33Y 80/00* (2015.01)
*B29L 31/00* (2006.01)
*B29K 705/00* (2006.01)
*B22F 3/24* (2006.01)

(52) U.S. Cl.
CPC ..... *B22F 2003/247* (2013.01); *B29K 2705/00* (2013.01); *B29L 2031/7546* (2013.01); *B33Y 10/00* (2014.12); *B33Y 80/00* (2014.12); *Y02P 10/295* (2015.11)

(58) Field of Classification Search
CPC .... A61B 2018/0275; A61B 2018/0281; A61B 2018/0287; A61B 2018/0293
See application file for complete search history.

(56) References Cited

U.S. PATENT DOCUMENTS

| | | |
|---|---|---|
| 2009/0082767 A1 | 3/2009 | Unger et al. |
| 2010/0268067 A1* | 10/2010 | Razzaque .......... A61B 18/1477 600/424 |
| 2011/0073246 A1 | 3/2011 | Brandt et al. |
| 2011/0288369 A1* | 11/2011 | Ginnebaugh ........ A61B 18/085 600/36 |
| 2012/0083786 A1 | 4/2012 | Artale et al. |
| 2012/0259331 A1 | 10/2012 | Garrison |
| 2014/0100568 A1* | 4/2014 | Garrison .............. A61B 18/085 606/45 |
| 2014/0353869 A1* | 12/2014 | Goodman .......... A61B 18/1442 264/104 |

FOREIGN PATENT DOCUMENTS

| | | |
|---|---|---|
| AU | 2013230575 A1 | 9/2014 |
| BR | PI 1107044 A2 | 1/2016 |
| CA | 2 754 243 A1 | 4/2012 |
| CA | 2 865 579 A1 | 9/2013 |
| CN | 102525639 A | 7/2012 |
| CN | 103717162 A | 4/2014 |
| CN | 104302239 A | 1/2015 |
| CN | 102525639 B | 11/2015 |
| CN | 105055020 A | 11/2015 |
| EP | 2 301 467 A1 | 3/2011 |
| EP | 2 436 330 A1 | 4/2012 |
| EP | 2 510 896 A1 | 10/2012 |
| EP | 2554132 A1 | 2/2013 |
| EP | 2 436 330 B1 | 11/2013 |
| EP | 2 671 528 A2 | 12/2013 |
| EP | 2 807 988 A1 | 12/2014 |
| EP | 2 822 495 A1 | 1/2015 |
| EP | 2 822 495 A4 | 10/2015 |
| EP | 2 671 528 A3 | 7/2016 |
| EP | 3 045 135 A1 | 7/2016 |
| JP | 5-291746 A | 11/1993 |
| JP | H 09-223428 A | 8/1997 |
| JP | 9-260013 A | 10/1997 |
| JP | 2002-301162 A | 10/2002 |
| JP | 2006-247972 A | 9/2006 |
| JP | 2012-75906 A | 4/2012 |
| JP | 2013/141606 A | 7/2013 |
| JP | 5789470 B2 | 10/2015 |
| KR | 10-2012-0035129 A | 4/2012 |
| RU | 2 234 282 A | 1/2004 |
| WO | WO 02/080785 A1 | 10/2002 |
| WO | WO 2013/134044 A1 | 9/2013 |

* cited by examiner

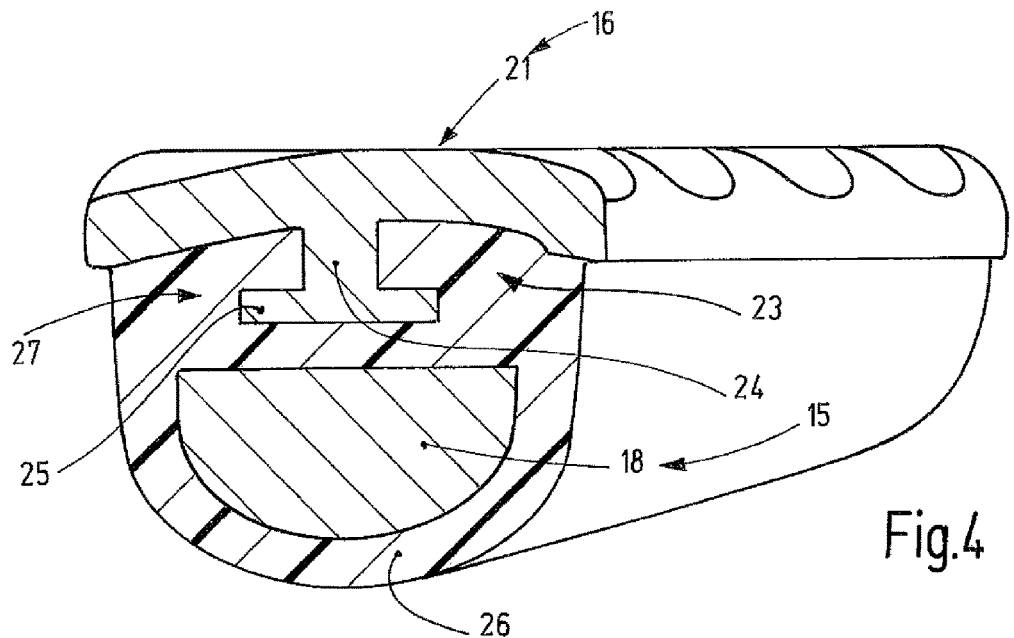
Fig.4
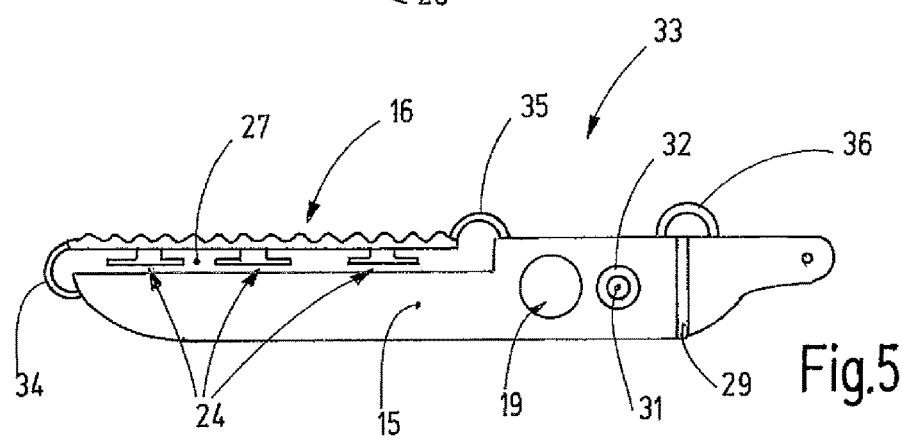
Fig.5
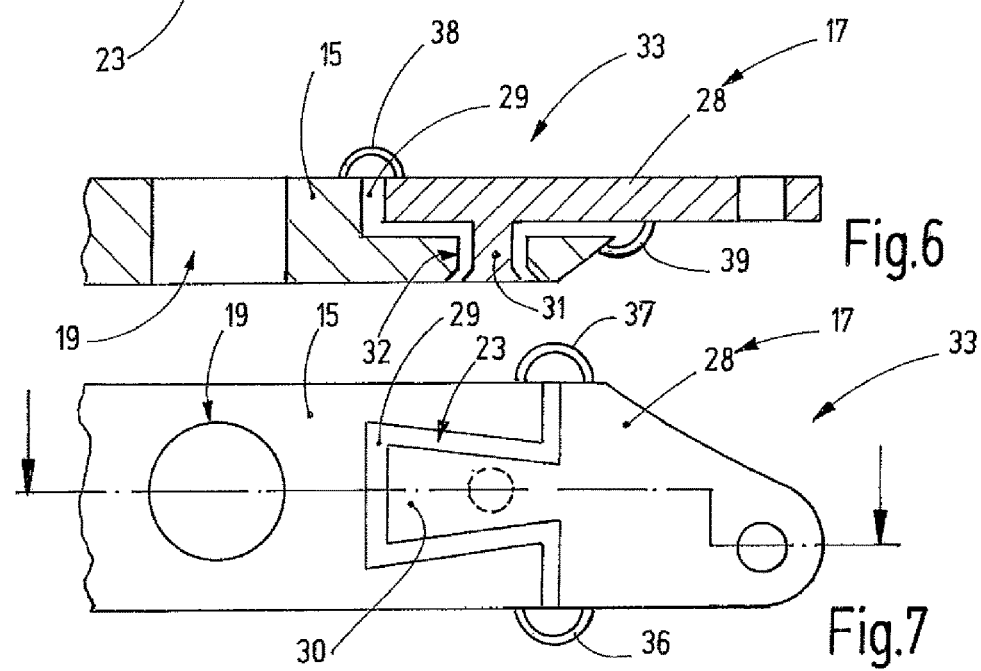
Fig.6
Fig.7

METHOD FOR PRODUCING A BRANCH AND SURGICAL INSTRUMENT COMPRISING A TOOL HAVING A BRANCH

TECHNICAL FIELD

Embodiments of the invention relate to a method for producing a branch for a surgical instrument and an instrument having at least one branch provided by means of the method.

BACKGROUND

Document EP 2 554 132 discloses an instrument for the coagulation of biological tissue between two branches of a tool of a surgical instrument. Each branch comprises an electrode support, which is connected to a thin, plate-shaped electrode via a plurality of punctiform welded connections. The electrode support can have a plastic housing.

Furthermore, US 2011/0073246 A1 discloses an instrument having branches comprising a plastic-metal composite part. This is formed by an electrode plate having a U-bent edge, which has circumferential recesses or holes. Plastic is injected beneath the electrode plate and extends over the edge of the electrode plate.

Furthermore, WO 02/080785 A1 relates to the anchoring of electrode plates in an electrically insulating substrate for branches of a medical instrument. The electrode plate can have an offset edge, which is in form-locked engagement with the plastic substrate.

When designing medical instruments for coagulating tissue, it should be ensured that the tongs-like tool is precisely designed and can apply relatively high pressure on biological tissue. Additional restrictions, such as sterility, sterilizability, heat resistance, electrical insulation of the electrode plates, thermal insulation of the electrode plates with respect to the surrounding tissue, etc., must also be taken into consideration.

SUMMARY

Proceeding therefrom, the object of embodiments of the invention is to specify a concept for producing improved branches for producing high-quality medical instruments.

In an embodiment of the invention, a metal part is initially provided, which has a support section and a functional section, which are intended to be electrically insulated from one another on the finished branch, but which are initially connected to one another as one piece via an electrically conductive connecting web. This metal part is encapsulated in plastic via injection-molding, wherein at least one surface region of the functional section can be left exposed, which is preferably the case. Preferably, the connecting web is also left at least partially exposed. The plastic establishes a mechanical connection between the support section and the functional section, i.e., it touches both sections and thereby forms a bonded and/or form-locked connection. Once said mechanical connection has been established, the connecting web is removed. In this case, if the connecting web was also encapsulated in plastic via injection molding, the plastic can also be partially removed. If the connecting web was left exposed, it can be removed without the surface of the plastic being penetrated. The connecting web can be removed by means of cutting, breaking off, grinding, laser cutting, or any other suitable separating method.

After the connecting web or connecting webs are removed, the support section and the functional section are electrically separated from one another. Due to the plastic connection, however, they remain fixedly interconnected and thereby form a largely gap-free, compact component. Given that there is no metallic connection between functional sections, support sections, these are not only electrically insulated from one another, but the heat transfer between the functional section and the support section is reduced.

In an another embodiment, the metal part is provided in a primary shaping process for example in an additive production process, for example by adding liquid metal droplets locally to an existing metal part in order to build up the metal part. As an alternative, the metal part can be produced in a casting process, for example a precision-casting process or metal injection molding (MIM). In a preferred embodiment, the metal part is provided by means of a powder metallurgical production process, for example by means of selective laser melting of metal powder. The metal part is created layer-by-layer via laser melting in a bed of metal powder. Complicated geometries having numerous undercuts, narrow gaps, and the like can be produced in this manner. Other 3D printing methods can also be used to manufacture metal parts.

The functional section of the branch can be an electrode plate, a lever arm, or any other type of section, which must be electrically and/or thermally separated from the support section, but which is connected thereto in a mechanical or form-locked manner and/or a bonded manner.

The functional section and the support section are preferably provided such that they form a gap with one another. This gap is preferably completely filled with a material, for example a plastic. In the gap, holding structures can be formed on the functional section and/or on the support section, said holding structures extending in the direction toward the respective other section, but not coming into contact therewith. The holding structures are preferably undercut structures, for example hook shapes, T-structures, mushroom head structures, hammerhead structures, or the like. This makes it possible, in particular, to anchor the section having an exposed surface region, in particular the functional section, in the plastic in a form-locked manner. The support section can comprise such structures or can be entirely encased in plastic, whereby in turn the plastic is anchored on the support section in a form-locked manner. The material used to connect the functional section and the support section can comprise components that enable a bonded connection between the functional section and the support section. It is thereby possible to connect the functional section and the support section to one another in a form-locked and/or bonded manner.

The electrosurgical instrument according to an embodiment of the invention comprises at least one branch, which has a support section and a functional section, which are made of metal having the same composition and structure, and which are fixedly interconnected via a body, preferably a plastic body. The reason why the composition and structure of the metal are the same is preferably because the support section and the functional section were jointly produced in a single primary shaping process, wherein connection webs were provided during the production of the support section and the functional section, which were removed after the gap was filled and/or the metal part was encapsulated with the connection material, for example the plastic, via injection molding. The support section and the functional section are therefore parts of a component that was previously a seamless, single component.

The functional section, which can be an electrode plate, a lever arm, or the like, is embedded together with the support section in a body and is anchored therein in a form-locked and/or bonded manner. Holding structures can be provided therefor, for example projections extending into the gap. One or more such projections can be arranged on the side of the functional section facing the holding section. In addition or as an alternative thereto, one or more such projections can be arranged on the side of the holding section facing the functional section. At least one of the projections preferably has an undercut. It is thereby ensured that a secure, loadable connection, which is resistant to changes in temperature, exists between the functional section and the support section even after the connecting webs have been removed.

Further details of advantageous embodiments of the invention are the object of the drawing, the description, or claims.

BRIEF DESCRIPTION OF THE DRAWINGS

FIG. 4 shows the branch according to FIGS. 2 and 3, in cross section;

FIG. 5 shows a metal part for forming the branch according to FIGS. 2 through 4, in schematic side view;

FIG. 6 shows the metal part according to FIG. 5 in enlarged illustration, in exposed sectional top view; and FIG. 7 shows the metal part according to FIGS. 5 and 6, in rear sectional view.

DETAILED DESCRIPTION

Figure 1:
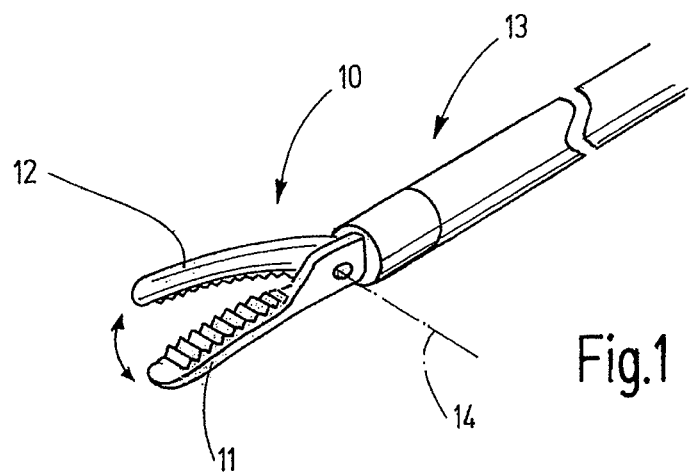
FIG. 1 shows an instrument according to an embodiment of the invention in schematic perspective sectional illustration.

FIG. 1 shows the tool part 10 of a surgical instrument, which is used to coagulate tissue gripped between two branches 11, 12 of the tool part 10. The tool part 10 is mounted on a shaft 13, through which at least one actuation element for the tool part 10 extends, by means of which at least one of the branches 11, 12 is movable, in particular being pivotable about an axis 14.

Figure 2:
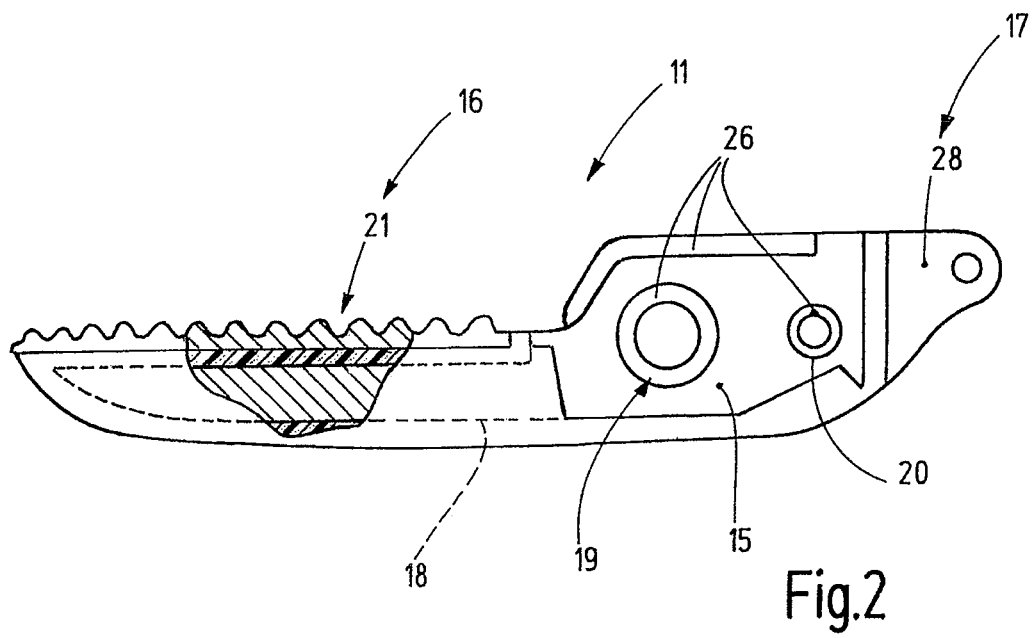
FIG. 2 shows a branch of a tool of the instrument according to FIG. 1, in partially exposed simplified side view.

FIG. 2 illustrates the branch 11 as an example. The branch 12 preferably has the same structural design such that the following description applies similarly for the branch 12.

In one embodiment, the branch 11 is a plastic-metal composite part. It includes a support section 15 and at least one, in the present case two functional sections 16, 17. The support section 15 comprises an elongate finger 18, which is illustrated with dashed lines in FIG. 2 and which is rigid in order to absorb the forces occurring on the branch 11. A hinge opening 19, in addition to other structures, can also be formed in the support section 15, for example in the form of a passage opening 20, for example for fastening further parts.

Figure 3:
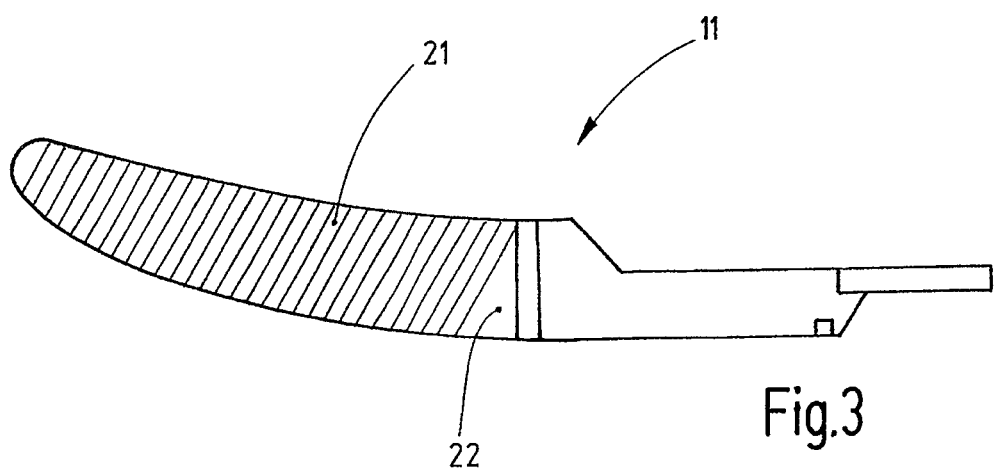
FIG. 3 shows another embodiment of the branch according to FIG. 2, in top view.

In the present exemplary embodiment, the functional section 16 is formed by an electrode plate 21, which is intended to be brought into contact with the biological tissue to be coagulated. The electrode plate 21 has a functional surface, which can be flat or, as illustrated in FIGS. 1 and 2, can be provided with a structure for example in the form of a row of transverse ribs. The functional surface is exposed on the finished branch 11 such that it can come into contact with tissue. The electrode plate 21 can be straight or, as illustrated in FIG. 3, can be curved along the longitudinal direction thereof. The electrode plate 21 is preferably provided with connecting means (not illustrated) for the attachment of an electrical lead. In the simplest case, said electrical lead can be fastened, for example on a flat point 22 (FIG. 3) of the electrode plate 21 by means of point welding. Other connecting possibilities and embodiments are feasible. Functional surfaces covered with plastic can also be provided.

The functional section 16 can be provided with a holding structure 23, which is designed for example in the form of one or more projections 24. Such projections 24 preferably extend away from the side of the functional section 16 facing the support section 15, in the direction of the support section 15. The projections 24 can be continuous or can have an enlarged cross section at one or more points with increasing spacing from the functional section 16. FIG. 4 shows a stepwise cross-sectional enlargement, whereby the projection 24 forms a head 25. This head 25 forms an undercut as viewed from the finger 18. Said head is used to anchor the functional section 16 in a material, for example a material jacket, preferably a plastic jacket 26, which has been injection-molded around the support section 15. The thusly formed plastic jacket 26 fills, in particular, a gap 27 formed between the functional section 16 and the support section 15. The projections 24 extending into this gap 27 anchor the functional section 16 in the body of the plastic jacket 26 in a form-locked manner. The plastic jacket 26 is held on the support section 15 in a form-locked manner by engaging around said support section. The support section 15 and the functional section 16 are thermally and electrically separated from one another. There is no metallic bridge between the two.

The further functional section 17 of the branch 11 is a lever 28, for example, which is connected to the support section 15 in a mechanically fixed manner, but without electrical contact. The lever 28 extends in the direction opposite the finger 18, as viewed from the hinge opening 19. The lever 28 is used to introduce forces into the branch 11 in order to move said branch for example in the closing direction, in order to grip tissue. As necessary the lever 28 can also have an exposed surface region, for example as the functional surface, which is not encapsulated in plastic via injection-molding.

The design of the functional section 17 emerges, in particular, from FIGS. 5 to 7, which illustrate the branch 11 before application of the plastic jacket 26. In turn the functional section 17 and the support section 15, in combination with one another, define a gap 29, which is filled with a material in the subsequent production process. The gap can be straight or U-bent, offset or can any other type of geometrically complex shape. For example, said gap can have a dovetail-shaped contour, as shown in FIG. 7. Within said contour, a projection 30 of the functional section 17 or the lever 28 engages into a corresponding recess of the support section 15 in order to define the gap 29 as a meander. In addition, a projection 31 of the lever 28 directed transversely thereto can engage into a corresponding recess 32 of the support section 15. The gap 29 can therefore extend around the projection 31, which is cylindrical or mushroom-shaped, for example.

In one embodiment, the branch 11 is produced as follows:

Initially a metal part 33 is provided, as shown in FIGS. 5 to 7. This metal part 33 encloses the support section 15 as well as the functional sections 16, 17. The support section 15 is connected to the functional section 16 via at least one, preferably numerous connecting webs 34, 35. Likewise the functional section 17 is connected to the support section 15 via one or more connecting webs 36, 37, 38, 39. In order to manufacture the metal part 33, suitable primary shaping processes are preferably used, in particular suitable additive production processes, such as for example selective laser melting, 3D printing or other powder metallurgical processes, such as for example the MIM process, in which the desired metal part 33 is produced entirely as a single piece having a uniform structure and composition. In a subsequent production step, the metal part 33 is provided with the material jacket 26 in a suitable tool. Said material jacket also enters the gap 27, 29, in particular, and seals said gap with respect to the outside. The gaps 27, 29 are preferably completely filled with the material. In addition, the hinge opening 19 can be completely or partially filled. For example a dimensionally-stable bearing bore can be formed by means of a mold core. The tool for applying the material can be a plastics injection mold, and the material can be a plastic.

After the plastic jacket 26 has cured, the connecting webs 34 to 39 are removed. Depending on the material properties, said connecting webs can be cut off, broken off, torn off, or removed by any other means, for example by laser processing, punching, grinding, or milling. This applies for embodiments of the method, in which the connecting webs 34 to 39 are located outside of the material jacket 26, and in methods that leave material on the connecting webs 34 to 39.

The branch 11, according to an embodiment of the invention, is created by means of an additive 3D production process for producing a metal part 33, which comprises at least two sections, namely a support section 15 and a functional section 16, 17. The metal part 33 is a single-pieced part, in which the support section 15 and the functional section 16, 17 are seamlessly interconnected by means of corresponding connecting webs 34, 35. After the material 26 is applied, the connecting webs are removed. The thusly produced branch 11 is dimensionally accurate, compact, and has excellent electrical and thermal and mechanical properties.

What is claimed as new and desired to be protected by Letters Patent of the United States is:

1. A method for producing a branch for a surgical instrument, the method comprising:
    forming a support piece, at least one electrode and at least one connecting web as a one-piece metal part in an additive production process, the support piece being configured to provide structural support for the branch and being interconnected with the at least one electrode via the at least one connecting web, the support piece, the at least one electrode and the at least one connecting web each comprising a first material;
    encapsulating the metal part with a second material; and
    removing the at least one connecting web.

2. The method of claim 1, wherein the one-piece metal part is provided by means of selective laser melting of metal powder.

3. The method of claim 1, wherein the encapsulating step comprises leaving at least one surface region of the at least one electrode exposed.

4. The method of claim 3, wherein the support piece and the at least one electrode, in combination with one another, form a gap, wherein at least one holding structure is formed on the at least one electrode, wherein said at least one holding structure does not touch the support piece.

* * * * *